(12) United States Patent
Cular

(10) Patent No.: US 8,018,121 B1
(45) Date of Patent: Sep. 13, 2011

(54) INTEGRATED THICKNESS SHEAR MODE (TSM) SENSOR AND SURFACE ACOUSTIC WAVE (SAW) DEVICE FOR SIMULTANEOUS SENSING AND REMOVAL OF ANALYTES

(75) Inventor: Stefan Cular, Alexandria, VA (US)

(73) Assignee: University of South Florida, Tampa, FL (US)

( * ) Notice: Subject to any disclaimer, the term of this patent is extended or adjusted under 35 U.S.C. 154(b) by 106 days.

(21) Appl. No.: 12/483,456

(22) Filed: Jun. 12, 2009

Related U.S. Application Data

(60) Provisional application No. 61/060,966, filed on Jun. 12, 2008.

(51) Int. Cl.
*H01L 41/08* (2006.01)
(52) U.S. Cl. .................................. 310/313 R
(58) Field of Classification Search .............. 310/313 R, 310/313 D; 71/53.01; *H01L 41/08*
See application file for complete search history.

(56) References Cited

U.S. PATENT DOCUMENTS

| 6,407,479 | B1 | 6/2002 | Moellendorf et al. | |
|---|---|---|---|---|
| 7,134,319 | B2 | 11/2006 | Liu | |
| 2005/0016276 | A1* | 1/2005 | Guan et al. | 73/579 |
| 2007/0107498 | A1* | 5/2007 | Thotadakumbri et al. | 73/53.01 |
| 2009/0151428 | A1* | 6/2009 | Bhethanabotla et al. | 73/24.06 |

OTHER PUBLICATIONS

Cular, et al., Removal of Nonspecifically Bound Proteins on Microarrays Using Surface Acoustic Waves, IEEE Sensors Journal, Mar. 2008, vol. 8, No. 3, pp. 314-320.

Cular, et al., Hexagonal Saw Interleukin-6 Biosensor, American Institute of Chemical Engineers Annual Meeting, Nov. 2007, Salt Lake City, Utah.

Cular, et al., Removal of Nonspecific Binding on Microsensors Using Surface Acoustic Waves, American Institute of Chemical Engineers Conference, 2005, Cincinnati, Ohio.

Cular, et al., Acoustic Manipulation of Biological Samples for Improved Sensors, American Institute of Chemical Engineers Conference, 2005, Cincinnati, Ohio.

Cular, et al., Hexagonal Surface Acoustic Wave Devices for Enhanced Sensing and Materials Characterization, American Institute of Chemical Engineers Conference, 2005, Cincinnati, Ohio.

Grant D. Meyer, Jose M. Moran-Mirabal, Darren W. Branch, and Harold G. Craighead, Nonspecific Binding Removal From Protein Microarrays Using Thickness Shear Mode Resonators, IEEE Sensors Journal, vol. 6, No. 2, Apr. 2006.

(Continued)

*Primary Examiner* — Walter Benson
*Assistant Examiner* — Karen Addison
(74) *Attorney, Agent, or Firm* — Courtney M. Dunn; Smith & Hopen, P.A.

(57) ABSTRACT

Provided is a sensor which integrates a pair of substantially unidirectional surface acoustic wave (SAW) interdigital transducers (IDTs) and a thickness shear mode (TSM) electrode. The sensor provides simultaneous sensing and removal of material from the sensor's surface. The sensing aspect is accomplished through the use of the TSM electrode that is designed to operate between 2 and 100 MHz. The removal of material is accomplished using substantially unidirectional IDTs aligned on the substrate to produce acoustic waves, such as Rayleigh waves, across the entire TSM sensor active area. When liquid is added over the acoustic waves, acoustic streaming occurs, which dislodges material from the sensor's surface. The acoustic waves are designed to operate at a significantly different frequency than the sensor to prevent interference between the two.

9 Claims, 2 Drawing Sheets

OTHER PUBLICATIONS

Stefan Cular, Venkat R. Bhethanabotla, Darren W. Branch, Simultaneous Surface Manipulation and Sensing in a Biosensor Using a Hexagonal SAW Device, presented at AIChE Annual Meeting, San Francisco, CA, USA, 2006.

Stefan Cular, V. R Bhethanabotla, and D.W. Branch, Vapor Discrimination Using a Hexagonal Surface Acoustic Wave Device, presented at IEEE Ultrasonics Symposium, Vancouver, CA, 2006.

* cited by examiner

INTEGRATED THICKNESS SHEAR MODE (TSM) SENSOR AND SURFACE ACOUSTIC WAVE (SAW) DEVICE FOR SIMULTANEOUS SENSING AND REMOVAL OF ANALYTES

CROSS REFERENCE TO RELATED APPLICATIONS

This application claims priority to co-pending U.S. Provisional Patent Application No. 61/060,966, filed Jun. 12, 2008.

STATEMENT OF GOVERNMENT INTEREST

This invention was made with Government support under Contract Number W81XWH-05-1-0585 awarded by the United States Army and Grant Number DGE-0221681 awarded by the National Science Foundation. The Government has certain rights in the invention.

FIELD OF INVENTION

This invention relates to thickness shear mode sensors and surface acoustic wave devices. More specifically, this invention relates to a device that simultaneously senses concentrations in complex fluids as well as removes material from the surface.

BACKGROUND

Sensors, including biosensors, are constantly hindered by the effects of fouling and non-specific binding of proteins. Non-specifically bound (NSB) protein interactions can interfere with sensor response and concentration determination. NSB protein interaction can cause, among other problems, reduced signal to noise ratios, exaggerated response due to multi-layer formation, false responses due to miscellaneous proteins covering the surface, and no response due to poor alignment of the functional groups. Minor improvements to biosensor responses can be achieved by a thorough rinsing, use of ultrasonic baths, and pretreatment of the analyte containing fluids. However, each of these processes adds to the complexity of the creation and use of the biosensor and decreases the functionality of a biosensor operated without specialized training in everyday environments. Developments in acoustic wave applications have demonstrated NSB protein removal with relatively low power consumption thus significantly decreasing the uncertainty of the sensors response.

SAW devices known in the art lack the ability to remove NSB proteins while also detecting biological species. An improved sensor is needed in the art that provides simultaneous sensing and removal of NSB proteins. The improved sensor needs to improve sensitivity and selectivity while simultaneously removing NSB proteins. However, in view of the prior art considered as a whole at the time the present invention was made, it was not obvious to those of ordinary skill in the pertinent art how the identified need could be fulfilled.

SUMMARY OF THE INVENTION

The need for a sensor that exhibits desired characteristics superior to sensors known in the art is now met by a new, useful, and non-obvious invention.

In accordance with the present invention a sensor is provided including a substrate, a pair of surface acoustic wave (SAW) interdigital transducers (IDTs) on the substrate, and a thickness shear mode (TSM) electrode on the substrate. The SAW IDTs are aligned in a substantially unidirectional manner. The pair of SAW IDTs is also arranged to form an acoustic path capable of propagating an acoustic wave therebetween. The TSM electrode lies in between the SAW IDT pair in the acoustic path.

In an embodiment, the sensor also has a second TSM electrode located on a second side of the substrate.

In an additional embodiment, the substrate is selected from the group consisting of quartz, lithium niobate, lithium tantalate, and langasite.

In a further embodiment, the SAW IDTs are of sufficient size to expose the entire surface of the TSM electrode to the acoustic wave.

Also provided in accordance with present invention is a method for simultaneous sensing and removal of materials from a sensor's surface. The method includes providing a sensor as described above, operating the TSM electrode between 2 and 100 Mhz, producing acoustic waves along the acoustic path and across the TSM electrode, and adding a liquid over the acoustic wave to induce acoustic streaming. The acoustic wave is produced using the pair of SAW IDTs. The operation of the TSM electrode provides the sensing for the device while the SAW IDT pair provides for the acoustic streaming, which dislodges analytes from the sensor's surface.

In an embodiment, the acoustic waves are Rayleigh waves.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention capitalizes on the ease of use of a thickness shear mode (TSM) sensor, such as quartz crystal microbalances, and the lower power required by a surface acoustic wave (SAW) device to remove material from the surface. The combination of these two devices provides a novel device that has stable, easy to operate sensing and reduces the effects caused by fouling analytes. The device is also able to regenerate itself for repeated/continual sensing use.

Figure 1:
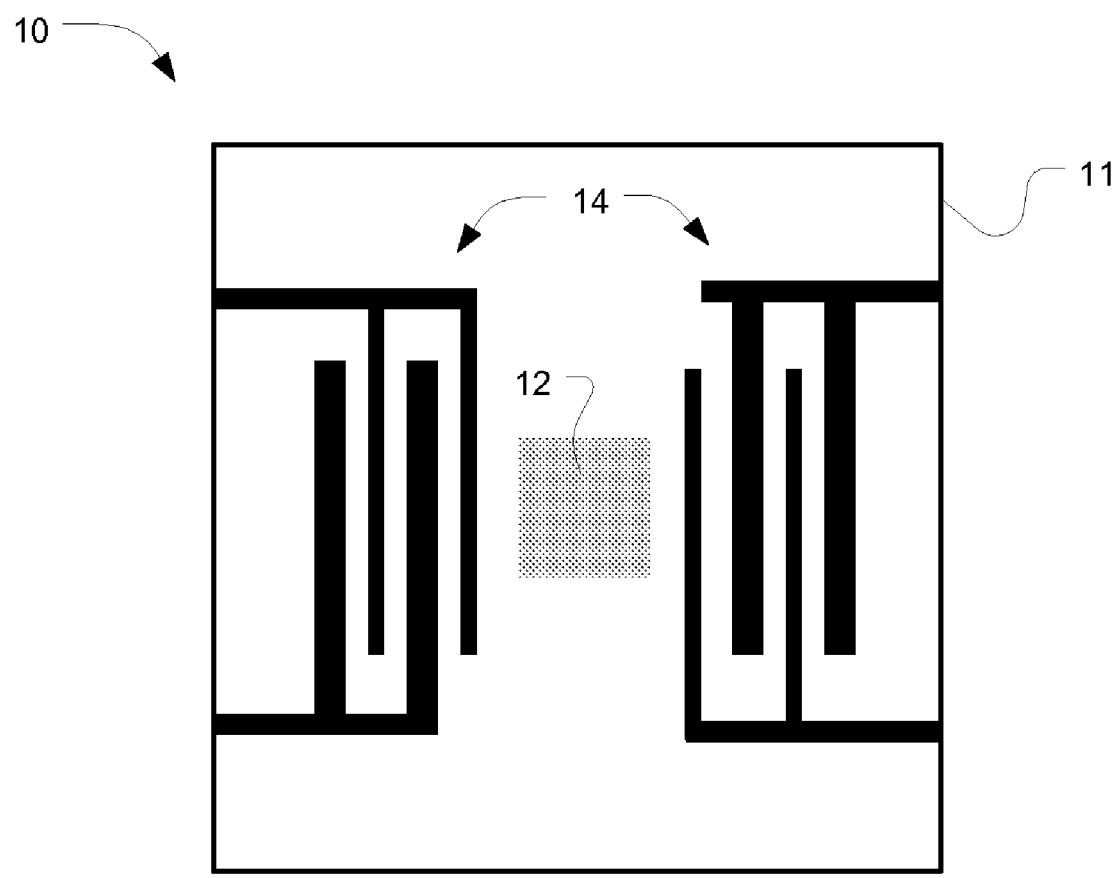
FIG. 1 is a schematic diagram of a first side of an integrated thickness shear mode (TSM) sensor and surface acoustic wave (SAW) device for simultaneous sensing and removal of analytes in accordance with an embodiment of the present invention.
Figure 2:
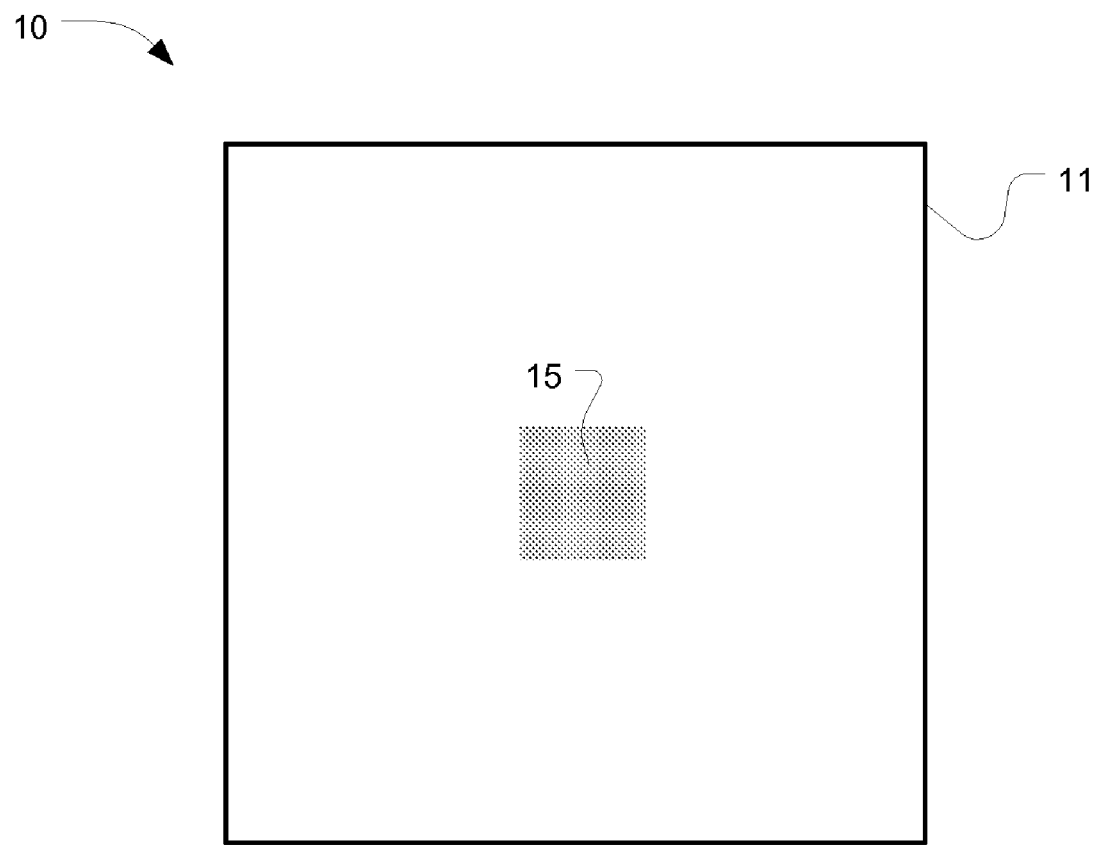
FIG. 2 is a schematic diagram of a second side of the integrated TSM sensor and SAW device for simultaneous sensing and removal of analytes in accordance with an embodiment of the present invention.

As shown in FIG. 1, sensor 10 comprises piezoelectric substrate 11, pair of SAW interdigital transducers (IDTs) 14, and thickness shear mode (TSM) electrode 12. SAW IDT pair 14 and TSM electrode 12 are located on the top surface of substrate 11. Second TSM electrode 15 may also be located on the bottom surface of substrate 11, as shown in FIG. 2.

Sensing is accomplished through the use of TSM electrode 12 which preferably operates between 2 to 100 MHz and is functionalized using methods known in the art, both depending on the specific application.

Removal of material is accomplished using pair of SAW IDTs 14. SAW IDTs 14 are designed such that they are at least substantially unidirectional. SAW IDTs 14 are also aligned on substrate 11 to create an acoustic path between SAW IDT pair 14. SAW IDT pair 14 is capable of propagating acoustic waves along this acoustic path. In a preferred embodiment, the acoustic waves are Rayleigh waves. When liquid is added over the acoustic waves, a phenomena known as acoustic streaming occurs that is sufficient to dislodge material from the surface of substrate 11. The acoustic waves are designed to operate at a significantly different frequency than the sensor to prevent any interference between the two.

In a preferred embodiment, SAW IDT pair 14 are of sufficient size and aligned in a manner such that the acoustic waves produced by SAW IDT pair 14 are propagated across the entire active area of TSM electrode 12. SAW IDT pair 14 is also designed such that each IDT is substantially unidirectional. This allows the most possible acoustic wave energy to the surface of TSM electrode 12.

In an embodiment, piezoelectric substrate 11 is double polished. Piezoelectric substrate 11 may be any known in the art and may selected according to a particular application. For example, quartz, such as ST-cut quartz or AT-cut quartz for temperature stabilization, may be used. Other examples include lithium niobate, lithium tantalate, and langasite.

The TSM electrodes and the SAW IDTs are added to the surface of the substrate through standard lithographic techniques. The electrodes and transducers may be made using a titanium adhesion layer with gold on top. However, these materials are not meant to be limiting; other metals and conductors may be used, and a thin layer of oxide or polymer may be added to provide needed sensor characteristics to functionalize the sensor surface.

The operation of the TSM electrode 12 is controlled with a well-known oscillator circuit. The operation of the SAW component is accomplished with a frequency generator and a power amplifier that can be tuned to the desired energy. Both IDTs in the IDT pair are powered when the device is operating.

The surface acoustic waves from the IDTs can be used for many functions. Examples include:

1) Run with lower power while the TSM electrode(s) is working to increase the mass transfer to the sensor surface and decrease fouling;
2) Run with higher power after the TSM electrode(s) has been used for a measurement to regenerate the surface; and
3) Run with medium power after the TSM electrode(s) surface has collected material. This will remove material in order from weakest to strongest affinity and will result in spectral type data.

The present invention is described with reference to biosensors; however, it can be used for chemical sensors as well. As a biosensor, the device can be used as an analytical instrument for consumer use. Also, because the sensor is not susceptible to fouling, it can be used in industrial processes for such things as viscosity measurements.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A sensor, comprising:
   a substrate;
   a pair of substantially unidirectional surface acoustic wave (SAW) interdigital transducers (IDTs) on the substrate aligned to create an acoustic path that propagates an acoustic wave therebetween; and
   a thickness shear mode (TSM) electrode on the substrate positioned in the acoustic path between the pair of SAW IDTs.

2. The sensor of claim 1, further comprising:
   a second TSM electrode on a second side of the substrate.

3. The sensor of claim 1, wherein the substrate is selected from the group consisting of quartz, lithium niobate, lithium tantalate, and langasite.

4. The sensor of claim 1, wherein the IDTs are of sized to expose the entire surface of the TSM electrode to the acoustic wave.

5. A method of simultaneously sensing a material and removing analytes from a sensor's surface comprising:
   providing a sensor comprising:
      a substrate,
      a pair of substantially unidirectional SAW IDTs on the substrate aligned to create an acoustic path that propagates an acoustic wave therebetween, and
      a TSM electrode on the substrate positioned in the acoustic path between the pair of SAW IDTs;
   operating the TSM electrode between 2 and 100 MHz whereby sensing of the material occurs;
   producing acoustic waves along the acoustic path and across the TSM electrode using the pair of SAW IDTs; and
   adding a liquid over the acoustic waves to induce acoustic streaming whereby analytes are dislodged from the sensor's surface.

6. The method of claim 5, wherein the sensor further comprises a second TSM electrode on a second side of the substrate.

7. The method of claim 5, wherein the substrate of the sensor is selected from the group consisting of quartz, lithium niobate, lithium tantalate, and langasite.

8. The method of claim 5, wherein the IDTs of the sensor are sized to expose the entire surface of the TSM electrode to the acoustic wave.

9. The method of claim 5, wherein the acoustic waves are Rayleigh waves.

* * * * *